United States Patent [19]

Shimamoto et al.

[11] 4,182,876
[45] Jan. 8, 1980

[54] SUBSTITUTED-PHTHALAZONE 7-CARBOXYLIC ACID AND SALTS AND PROCESS FOR PREPARING SAME

[76] Inventors: Takio Shimamoto, No. 13, Kita-machi, Shinjuku-ku, Tokyo; Masayuki Ishikawa, No. 14-13, Akatsutsumi 3-chome, Setagaya-ku, Tokyo, both of Japan

[21] Appl. No.: 779,112

[22] Filed: Mar. 18, 1977

[30] Foreign Application Priority Data

Mar. 18, 1976 [JP] Japan .................................. 51/28592
Mar. 22, 1976 [JP] Japan .................................. 51/29815

[51] Int. Cl.$^2$ ..................... C07D 237/32; A61K 31/50
[52] U.S. Cl. ...................................... 544/237; 424/250
[58] Field of Search ..................... 260/250 P; 544/237

[56] References Cited

U.S. PATENT DOCUMENTS 3,864,343 2/1975 Inoue et al. ..................... 260/250 P
3,963,716 6/1976 Inoue et al. ..................... 260/250 P

OTHER PUBLICATIONS

Sandler et al., "Organic Function Group Preparations".

Primary Examiner—Mark L. Berch

Attorney, Agent, or Firm—Sughrue, Rothwell, Mion, Zinn and Macpeak

[57] ABSTRACT

Phthalazone derivatives of the formula

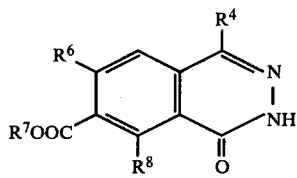

wherein $R^4$ represents a carbamoyl group, a dialkylaminoalkylcarbamoyl group, a hydroxyalkylcarbamoyl group, an alkylidenehydrazinocarbonyl group, a hydrazinocarbonyl group, an alkylhydrazinocarbonyl group, a formyl group, a hydrazonomethyl group, an alkylhydrazonomethyl group, a hydroxyiminomethyl group, a dialkylhydrazonomethyl group or an alkylidenehydrazonomethyl group; $R^6$, $R^7$ and $R^8$ each represent an alkyl group; and process for preparing same. The phthalazone derivatives are useful for the treatment and prevention of cerebral apoplexy, myocardial infarction and the like.

11 Claims, 1 Drawing Figure

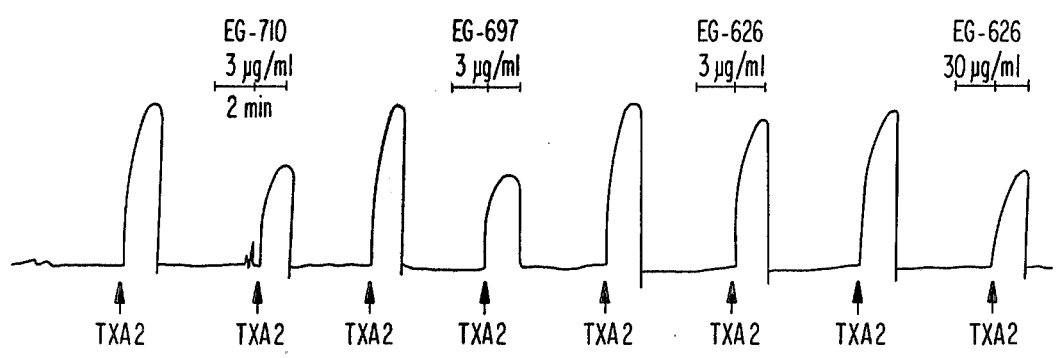

SUBSTITUTED-PHTHALAZONE 7-CARBOXYLIC ACID AND SALTS AND PROCESS FOR PREPARING SAME

BACKGROUND OF THE INVENTION

1. Field of the Invention

This invention relates to novel phthalazone derivatives and more particularly to compounds of the formula

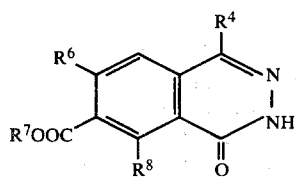

wherein $R^4$ represents a carbamoyl (—$CONH_2$) group, a dialkylaminoalkylcarbamoyl group, a hydroxyalkylcarbamoyl [—CONH(alkyl)OH] group, an alkylidenehydrazinocarbonyl [—CONHN=C(alkyl)$_2$] group, a hydrazinocarbonyl (—$CONHNH_2$) group, an alkylhydrazinocarbonyl (—CONHNHalkyl) group, a formyl (—CHO) group, a hydrazonomethyl (—CH=$NNH_2$) group, an alkylhydrazonomethyl [—CH=NNH(alkyl)] group, a hydroxyiminomethyl (—CH=NOH) group, a dialkylhydrazonomethyl [—CH=NN-(alkyl)$_2$] group, a carbamoylhydrazonomethyl (—CH=$NNHCONH_2$) group, or an alkylidenehydrazonomethyl [—CH=N—N=C(alkyl)$_2$] group; $R^6$, $R^7$ and $R^8$ each represent an alkyl group.

2. Description of the Prior Art

Since thromboxane $A_2$ was found by Dr. Samuelsson et al in 1974, it has been made clear that the substance is biosynthesized from prostaglandin endoperoxide ($PGG_2$ or $PGH_2$) by the action of an enzyme present in the platelets and thromboxane $A_2$ plays an important role on the subsistence of life in living body.

Thromboxane $A_2$ is regarded as one of the "local hormone" which appears at injured part in living body and the substance induces contraction of the blood vessels and aggregation of the platelets. Furthermore, it inhibits release of lipids such as cholesterol from the fat cells as well, and an assumption has been made as to thromboxane $A_2$ that the action is induced as a result of the decrease in C-AMP (adenosine cyclic monophosphate) concentration in the cells with thromboxane $A_2$. The intensity of these effects reaches as high as several hundred-fold of that led to with prostaglandin. These effects caused with thromboxane $A_2$ are supposed to be the cause of cerebral apoplexies (cerebral hemorrhage, cerebral thrombosis, etc.) myocardial infarction and as the main risk factor of arteriosclerosis. One of the present inventors has also confirmed that the intracarotid or intracoronary injection of thromboxane $A_2$ actually induces the experimental stroke or fatal or non-fatal myocardial infarction, respectively.

On the basis of the above supposition, the present inventors investigated to find thromboxane $A_2$ antagonist and reported on Proceedings of the Japan Academy, Vol. 52, No. 10 pages 591-594 (1976) that phthalazinol (6,8-dimethyl-7-ethoxycarbonyl-4-hydroxymethyl-1-phthalazone, EG-626) was effective. However, in order to get enough blood concentration, phthalazinol has to be given in a large dose, so that it is not yet satisfactory.

SUMMARY OF THE INVENTION

An object of this invention is to improve the above-described defects of the conventional thromboxane $A_2$ antagonist and to provide one having sufficient effect at a low dose.

Another object of this invention is to provide a thromboxane $A_2$ antagonist exhibiting satisfactory effect at a small dosage.

Yet another object of this invention is to provide a process for preparing phthalazone derivatives.

As a result of extensive research the present inventors synthesized novel phthalazone derivatives much more potent than phthalazinol and accomplished this invention.

The object compounds of this invention show antagonistic effect to thromboxane $A_2$ (TXA2) and they are expected to be useful for the treatment and prevention of cerebral apoplexy, myocardial infarction and the like.

BRIEF DESCRIPTION OF THE DRAWING

Single FIGURE is a graphical representation of effect of the compound of the present invention of the contraction of rabbit aorta strip.

DETAILED DESCRIPTION OF THE INVENTION

The term "lower alkyl group" used herein means an alkyl group having 1 to 6, preferably 1 to 3 carbon atoms. The novel phthalazone compounds are prepared by the following manner.

4-formyl-7-alkoxycarbonyl-6,8-dialkyl-1-phthalazone is prepared by the oxidation of the corresponding 4-hydroxymethyl compound. The oxidation is conducted using a suitable oxidizing reagent such as chromic acid or N-bromosucciinimide, and reaction condition may vary in some extent with the kind of the oxidizing reagent. When chromic acid salt or chromic anhydride is used, the oxidation proceeds under usual condition, for example, the oxidation is carried out with a combination of chromic salt such as sodium bichromate or potassium bichromate and sulfuric acid, or chromic anhydride and pyridine or sulfuric acid at 0°–50° C. When N-bormosuccinimide is used, it is preferable to add a radical generating reagent such as benzoyl peroxide. As another alternative method air oxidation in the presence of catalyst can be made as well.

Synthesis of the other compounds are illustrated by the following reaction equation.

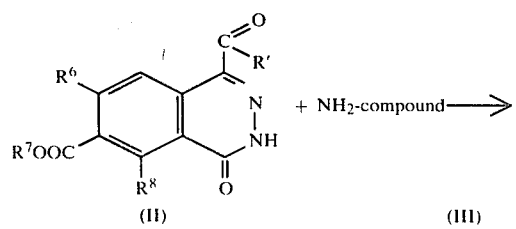

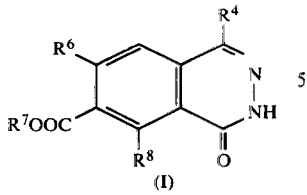

wherein $R^4$, $R^6$, $R^7$, and $R^8$ are the same as previously described, R' represents hydrogen or alkoxy.

As shown in the equaton, compound (I) is prepared by reacting 4-carbonyl compound (II) with $NH_2$-compound (III) such as ammonia, amines, hydrazines or hydrazones. More particularly, the $NH_2$-compound includes ammonia, hydroxylamine, hydrazine, monomethylhydrazine, dimethylhydrazine, semicarbazide, acetonehydrazone, methylethylketonehydrazone, ethylenediamine, N,N-dimethyl-ethylenediamine, N,N-diethyl-ethylenediamine, 1,3-diaminopropane, N,N-dimethyl-1,3-diaminopropane, N,N-diethyl-1,3-diaminopropane, 2-aminoethanol, 3-amino-1-propanol and the like.

When the starting material is 4-formyl-1-phthalazone derivative, the reaction is carried out in a suitable solvent or diluent such as water, methanol or ethanol. The $NH_2$-compound should be preferable to use 2 to 20-fold moles to the phthalazone and the reaction is desirably conducted with stirring at a temperature of 30°–150° C.

When the starting material is 4-alkoxycarbonyl phthalazone derivative [Japanese Patent Application (OPI) No. 70377/1975], the reaction is carried out usually in the absence of solvent or diluent, however, optionally it may be done in the presence of dioxane or the like. It is preferable to use equimolar to 20-fold moles of the $NH_2$-compound to the 4-alkoxycarbonyl-phthalazone and the reaction is preferably conducted with stirring at a temperature of 0°–50° C.

The content of the above-identified published Japanese Patent application (OPI) 70377/1975 is as follows:

| ⑲ JAPANESE PATENT OFFICE PUBLICATION OF UNEXAMINED PATENT APPLICATION | |
|---|---|
| ⑪ OPI Publication No. Sho 50-70377 | |
| ㊸ Date of Publication: June 11, 1975 | |
| ㉑ Japanese Patent Application No. Sho 48-121259 | |
| ㉒ Date of Application: October 30, 1973 | |
| Request for Examination: Not requested | |
| | (Total 5 pages) |
| Reference Numbers in the Patent Office 7306 44 7043 44 | |
| ㊼ Japanese Classification | ㊽ International Classification |
| 16 E 466 | CO7D237/32// |
| 30 B 0 | A61K 31/50 |
| Patent Application October 30, 1973 | |

To: Director-General,
   Patent Office:    Hideo Saito, Esq.
1. Title of the Invention:
   Method for Preparing Phthalazone Derivatives
2. Inventors:
   Address:
      Same as Applicant
   Name:
3. Applicant:
   Address: No. 6-26-3, Kokuryo, Chofu-shi, Tokyo, Japan
   Name: Michiro Inoue
   (Three other persons)
4. List of Documents Attached:

(1) Specification            1 copy
   (2) Duplicate of Patent Application    1 copy
5. Applicants Other Than Above:
   Address: No. 3-14-13, Akazutsumi, Setagaya-ku, Tokyo, Japan
   Name: Masayuki Ishikawa
   Address: No. 5-17-25, Minamikoiwa, Yodogawa-ku, Tokyo, Japan
   Name: Takashi Tsuchiya
   Address: No. 13; Kitamachi, Shinjuku-ku, Tokyo, Japan
   Name: Takio Shimamoto Specification 1. Title of the Invention
   Method for Preparing Phthalazone Derivatives
2. Scope of the Claim for Patent
   A method for preparing a 1-phthalazone-4-carboxylic acid derivative represented by the general formula

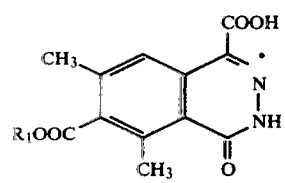

(wherein $R_1$ means an alkyl group) characterized by oxidizing a 3-hydroxyphthalide derivative of the general formula

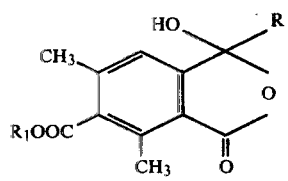

(wherein $R_1$ has the same meaning as above and R means an alkyl group) with a permanganate and reacting the resulting phthalonic acid derivative of the general formula

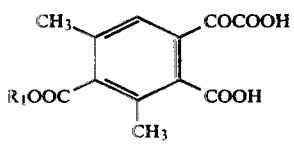

(wherein $R_1$ has the same meaning as above) with hydrazine.

3. Detailed Description of the Invention
   This invention relates to a method for preparing 1-phthalazone-4-carboxylic acid derivatives represented by the general formula

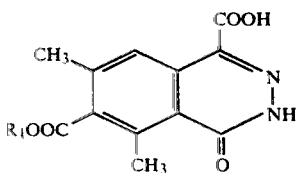

(wherein $R_1$ means an alkyl group).

According to this invention the compound of formula I is prepared by oxidizing a 3-hydroxyphthalide derivative of the general formula

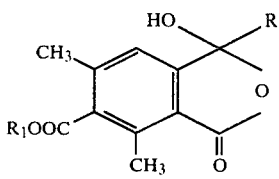

(wherein $R_1$ has the same meaning as above and R means an alkyl group) with a permanganate and reacting the resulting phthalonic acid derivative of the formula

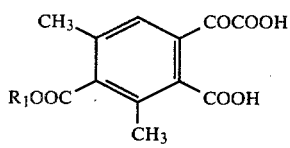

(wherein $R_1$ has the same meaning as above) with hydrazine.

As disclosed in the specification of the patent application (A) filed on the same day as the present application, the compound of the formula II used as starting material can be manufactured by reacting an acid anhydride of a 5-alkoxycarbonyl-4,6-dimethyl-1,2-dicarboxylic acid with a diethyl cadmium. The compound of formula II includes, for example, 4,6-dimethyl-7-ethoxycarbonyl-3-hydroxy-3-methylphthalide, 4,6-dimethyl-7-methoxycarbonyl-3-hydroxy-3-methylphthalide and the like. According to the disclosure in Journal of the Organic Chemistry, Vol. 32, page 3229, 1967, 3-hydroxy-3-methylphthalide is in a relation of tautomer with 2-acetylbenzoic acid, and, therefore, it is thought that the compound of formula II is first isomerized to a compound of formula II' having a 2-acylbenzoic acid structure under a basic condition as shown in the following scheme, and then the compound is oxidized.

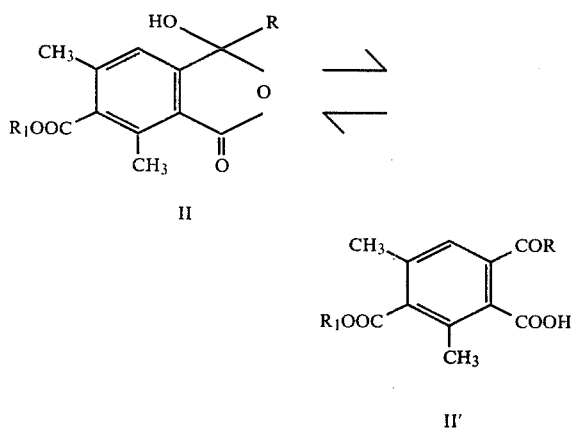

Firstly, the compound of formula II is oxidized with a permanganate in the presence of a neutral or basic substance. As the basic substance, sodium carbonate, potassium carbonate or potassium hydroxide, etc. can be used and as the permanganate, potassium permanganate, etc. can be used. Water can be used as a solvent, and the oxidizing reaction proceeds at a room temperature thereby yielding the compound of formula III in high yield. As far as 2 moles of a permanganate are used per mole of the compound of formula II, the two methyl groups directly connected to the benzol ring would never be oxidized. The compound of formula III is not necessary to be isolated from the oxidation reaction mixture and purified. When an equivalent or excess hydrazine is added to the reaction solution from which the precipitated brown solids have been removed and the mixture is kept at a temperature between 30° to 100° C. for several hours, the desired product of the formula I is produced in a good yield. In this case, the alkoxycarbonyl group is not reacted with hydrazine. The product can be isolated and purified by a usual manner.

The present invention is directed to a method for producing the compounds of formula I in high yield through simple operation. The compounds of formula I are novel compounds which are important as intermediates for the preparation of 6,8-dimethyl-4-hydroxymethyl-1-phthalazone-7-carboxylic acid alkyl esters useful for preventing arteriosclerotic diseases and thrombotic diseases.

Example (1) Preparation of 6,8-dimethyl-7-ethoxycarbonyl-1-phthalazone-4-carboxylic acid.

1.32 g of 5,7-dimethyl-6-ethoxycarbonyl-3-hydroxy-3-methylphthalide was dissolved in 100 ml of 1% potassium hydroxide aqueous solution. To the solution was added portionwise with stirring a solution of 1.58 g of potassium permanganate in 80 ml of water. Upon continuing the stirring at room temperature for additional 1.5 hour, the green color of the reaction solution was almost decolorized. The precipitated brown solids were removed by filtration and the filtrate was rendered weakly alkaline by introducing carbon dioxide gas thereinto. 5 ml of 80% hydrazine hydrate was added to the filtrate, and the mixture was heated at 70°–80° C. on a water bath for 2 hours. The cooled reaction mixture was rendered weakly acidic with dilute hydrochloric acid to precipitate crystals. The crystals were collected by filtration and recrystallized from methanol to obtain 1.1 g of 6,8-dimethyl-7-ethoxycarbonyl-1-phthalazone-4-carboxylic acid having a melting point of 216°–218° C. This compound had the following structure.

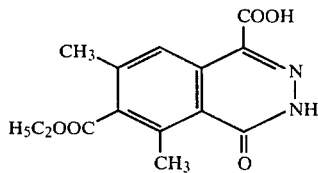

I.R. Spectrum: $\nu_{max}^{KBr}$ 1740, 1705, 1640 cm$^{-1}$

U.V. Spectrum: $\lambda_{max}^{EtOH}$ 220, 238 (shoulder), 262 (shoulder), 299, 310 (shoulder), 322 (shoulder) m$\mu$ This compound gives a diester when it is esterified in a usual manner as set forth below.

(2) Preparation of 6,8-dimethyl-1-phthalazone-4,7-dicarboxylic acid diethyl ester.

To a mixture comprising of 60 ml of absolute ethanol and 2 ml of concentrated sulfuric acid was added 700 mg of 6,8-dimethyl-7-ethoxycarbonyl-1-phthalazone-4-carboxylic acid produced by the procedure as described above, followed by boiling while refluxing on water bath for 5 hours. The reaction mixture was concentrated under reduced pressure, and the concentrated solution was diluted with water and extracted with chloroform. The chloroform extract was washed with an aqueous solution of sodium carbonate and then the chloroform was distilled off. The resulting residue was recrystallized from aqueous ethanol to obtain 600 mg of 6,8-dimethyl-1-phthalazone-4,7-dicarboxylic acid diethyl ester having a melting point of 159°–161° C.

IR Spectrum: $\nu_{max}^{KBr}$ 1740, 1660, 1370, 1265, 1110 cm$^{-1}$

U.V. Spectrum: $\lambda_{max}^{EtOH}$ 220, 240, 290, 309 (shoulder), 322 (shoulder) m$\mu$ Mass Spectrum: m/e 318 (M+), 289, 273 (end).

If the object compound is 4-alkylidenehydrazinecarbonyl compound [$R^4$=CONHN=C(alkyl)$_2$] or 4-alkylidenehydrazonomethyl compound [$R^4$=CH=NN=C(alkyl)$_2$], it is recommendable to prepare the compound through two steps i.e. reaction of 4-carbonyl compound with hydrazine to produce corresponding hydrazone or hydrazide and reaction of the resulting compound with ketones, such as acetone, methylethylketone and the like.

The desired compound (I) can be easily isolated or purified by conventional manners such as dilution with water, filtration, extraction or recrystallization. The compound is also able to be converted to salt form by a conventional manner, if desired and the salt will be sometimes useful in point of solubility.

The effect and activity of the present compound are very excellent and superior to phthalazinol. The details are described together with the biological test in the following.

(1) In an in vitro testing using Dr. Shibata's superfusion technique using rabbit-aortic strips, phthalazinol inhibits the isometric contraction of the aortic strip caused by thromboxane $A_2$ at a concentration of 30 $\mu$g/ml, however, the effect is not exactly led to at 10 $\mu$g/ml or below. On the other hand, it will be probably difficult to increase the blood level over 10 $\mu$g/ml unless a large dose is administered, so that it is apprehended that the effect is not adequately obtained in some clinical cases. While the novel compounds of this invention inhibit the contraction even at 3 $\mu$g/ml in the in vitro system of Dr. Shibata with rabbit-aortic strip, so it is expected effective in clinic even if the blood level does not reach at 10 $\mu$g/ml.

Biological Test

When thromboxane $A_2$ (TXA2) solution was added to rabbit aorta strip superfused in Krebs solution, strong contraction is induced. The inhibitory activity to the contraction of the representative compounds of this invention (EG-697; $R^4$=CONHNH$_2$, $R^6$=$R^8$=CH$_3$, $R^7$=C$_2$H$_5$ and EG-710; $R^4$=—CH=N—N=C(CH$_3$)$_2$, $R^6$=$R^8$=CH$_3$, $R^7$=C$_2$H$_5$) was evaluated by adding the drugs to the aorta strip bath before the addition of TXA2. The experiment was conducted according to the procedure of Dr. Shibata. This is a modified one of the method of Shimamoto et al [Proc. Japan Acad. Vol. 52, pages 591–594 (1976)]. The modification was made only in the manner for replacing the superfusate (Krebs solution containing TXA2 or the drug). The replacement was made in Shimamoto's method by continuous flow in and away of the liquid while by replacing all the required volume of the solution at a time in Shibata's method. The method of Shimamoto et al is also a modified method of Ellis' method [Science Vol. 193 pages 1135–1137 (1976) and Hamberg's method (Proc. Nat. Acad. Sci. USA Vol. 72, pages 2994–2998 (1975)].

As seen from Figure, the result indicates that the activity of inhibition with EG-697 or EG-710 at 3 $\mu$g/ml is almost equal to that of EG-626 at 30 $\mu$g/ml.

(2) The compounds of this invention prevent the experimental myocardial infarction and cerebral apoplexy in rabbit at approximately a tenth dose of phthalazinol.

Biological test

Experimental myocardial infarction and cerebral apoplexy were induced in male rabbits (2.0–2.85 kg) my injecting thromboxane $A_2$ (TXA2) mixture. The TXA2 mixture was prepared by adding thrombin to the washed rabbit platelets suspension. The number of platelets used was from $6 \times 10^8$ to $1.8 \times 10^9$ per ml and thrombin was added in a ratio of 1.5 units per $6 \times 10^8$ platelets per ml for the intra-coronary injection and in a ratio of 5 units per $1.8 \times 10^9$ platelets per ml for the intra-carotid injection. The mixture was used at exactly 20 second after the addition of thrombin. The concentration of TXA2 was measured using rabbit aortic strips and expressed in terms of norepinephrine or angiotensin II.

For the intra-coronary injection of TXA2 mixture (which induces cerebral apoplexy) catheter was inserted into the ascending aorta directly above the orifice of coronary arteries through the carotid artery under the light anesthesia with urethane. By inflation of balloon by 0.5 ml of air, the orifice area of the aorta was isolated for 3 second from the other part of aorta and the injection of 2 ml of TXA2 mixture containing 100–3000 ng/ml in terms of norepinephrine was successfully performed during that time into both coronary arteries. The ECG (electrocardiogram), EEG (electroencephalogram), blood pressure and respiration were recorded.

For the intra-carotid injection of TXA2 mixture, polyvinyl tube was connected to the right carotid artery by operation under the local anesthesia and through the tube the injection of 2 ml of TXA2 mixture containing 1500–3000 ng/ml of TXA2 in terms of angiotensin II was performed without anesthesia. The response of animals induced by this procedure was photographed by movie and the ECG, EEG, blood pressure and respiration were also recorded.

The each drug was given by intraperitoneal injection for the intra-carotid challenge and by intravenous injection for the intra-coronary challenge 1.5 to 5 hours before each challenge.

The animals received intra-coronary injection of TXA2 mixture exhibited a typical ECG-change of myocardial infarction, namely elevation of ST segment in precordial leads and broadening and deepening of the Q wave successively in the course of 5 to 24 hours.

On the other hand, the animals pretreated by intravenous injection of 1 mg/kg of EG-626 did not exhibit the myocardial infarction like change, while the cases pretreated with EG-697 or EG-710, the myocardial infarction were prevented in a dose of 0.1 mg/kg.

The animals received intra-carotid injection of TXA2 mixture exhibited stroke-like response such as generalized tonic and chronic convulsion, collapse or respiratory paralysis.

On the other hand, the animals pretreated by intraperitoneal injection of 10 mg/kg of EG-626 did not exhibit convulsion, collapse and paralysis, while the cases pretreated with EG-697 and EG-710 exhibited no behavioral response in a dose of 1 mg/kg.

From the experimental results described above, it is confirmed that the compounds of this invention is effective to prevent the experimental cerebral apoplexy and myocardial infarction in a dose of one-tenth of EG-626.

(3) The physiological importance of C-AMP has been enough known since the discovery of C-AMP by Southerland.

Recently, cyclic nucleotides, guanosine cyclic monophosphate (C-GMP) as well as C-AMP, attracted attention as intracellular messenger substance. Therefore, the action of thromboxane $A_2$ antagonist should be studied in connection with the concentrations of C-AMP and C-GMP, because some improper reaction might be taken place, if only the concentration of one of two nucleotide is increased. For example, when only C-AMP-PDE (adenosine cyclic monophosphate phosphodiesterase) in the cardiac muscle is inhibited it is supposed to cause amplification in the effect of adrenaline and noradrenaline system and some undesirable reactions might result in the circulating system.

Biological test

The effects of the novel compounds and EG-626 on C-AMP-PDE and C-GMP-PDE (guanosine cyclic monophosphate phosphodiesterase) were investigated according to the method of Hidaka et al [Biochimica et Biophysica Acta, Vol. 377 pages 103–116 (1975)]. The concentration of the drug to reduce the activity of C-AMP-PDE or C-GMP-PDE to the 50% level was measured and represented as $I_{50}$.

As shown in the following table, 20 μg of EG-626 reduced the activity of C-GMP-PDE to 50% but the activity of C-AMP-PDE was reduced to 50% by one-fortieth dose as compared with the case of C-GMP-PDE. This means that EG-626 effects far stronger to C-AMP-PDE than to C-GMP-PDE. While both enzymes were inhibited in almost equal degree by EG-697 and EG-710.

|  | $I_{50}$ (μg/assay) | | $I_{50}$ to C-GMP-PDE |
|---|---|---|---|
|  | C-AMP-PDE | C-GMP-PDE | $I_{50}$ to C-AMP-PDE |
| EG-626 | 0.5 | 20 | 40 |
| EG-697 | 12 | 22 | 1.8 |
| EG-710 | 0.5 | 0.5 | 1 |

EXAMPLE 1

7-ethoxycarbonyl-6,8-dimethyl-4-formyl-1-phthalazone ($R^4$=CHO, $R^6$=$R^8$=CH$_3$, $R^7$=C$_2$H$_5$).

To a solution of 4 g of 7-ethoxycarbonyl-6,8-dimethyl-4-hydroxymethyl-1-phthalazone and 100 ml of carbon tetrachloride, 3 g of N-bromosuccinimide and 40 mg of benzoyl peroxide were added. The resulting mixture was heated under reflux for 1.5 hours. After cooling, crystals precipitated were collected by filtration and recrystallized from acetone to give 2.7 g of crystals having m.p. 215°–217° C. On the other hand, the filtrate of the reaction mixture was concentrated in vacuo to remove carbon tetrachloride. When the residue was crystallized from aqueous acetone, 0.5 g of the second crop was obtained. Totally 3.3 g (83.1% in yield) of the desired product was obtained.

Analysis calculated for $C_{14}H_{14}N_2O_4$ C 61.31, H 5.15, N 10.21 found C 61.19, H 5.17, N 10.27; IR spectra ($\nu_{max}^{KBr}$): 1730, 1700, 1650 cm$^{-1}$.

EXAMPLE 2

4-hydrazonomethyl-6,8-dimethyl-7-ethoxycarbonyl-1-phthalazone ($R^4$=CH=NNH$_2$, $R^6$=$R^8$=CH$_3$, $R^7$=C$_2$H$_5$)

To a solution of 300 mg of 4-formyl-6,8-dimethyl-7-ethoxycarbonyl-1-phthalazone and 30 ml of ethanol, 500 mg of 80% hydrazine hydrate was added. The resulting mixture was stirred for one hour at room temperature and heated at 60° C. for additional one hour. The reaction mixture was concentrated in vacuo to about half volume. After cooling, the crystals precipitated were collected by filtration and recrystallized from methanol to give 260 mg of the desired product with m.p. 187°–189° C.

Analysis calculated for $C_{14}H_{16}O_3N_4$ C 58.32, H 5.59, N 19.44 found C 58.07, H 5.61 N 19.62, mass spectra (m/e): 188 (M+), 273, 259, 243, 231; IR spectra ($\nu_{max}^{KBr}$): 3400, 1730, 1640 cm$^{-1}$ By a similar manner as in Example 2 the compounds of Example 3 to Example 5 were obtained.

EXAMPLE 3

4-hydroxyiminomethyl-6,8-dimethyl-7-ethoxycarbonyl-1-phthalazone ($R^4$=CH=NOH, $R^6$=$R^8$=CH$_3$, $R^7$=C$_2$H$_5$) m.p. 207°–208° C.

(recrystallized from ethyl acetate)
mass spectra (m/e): 289, 273, 259, 243.
As the raw material, hydroxylamine was used.

EXAMPLE 4

4-dimethyl hydrazonomethyl-6,8-dimethyl-7-ethoxycarbonyl-1-phthalazone ($R^4$=CH=NN(CH$_3$)$_2$, $R^6$=$R^8$=CH$_3$, $R^7$=C$_2$H$_5$) m.p. 199°–201° C.

(recrystallized from methanol)
mass spectra (m/e): 316, 274, 258, 244.
As the raw material, unsym-dimethylhydrazine was used.

EXAMPLE 5

4-carbamoylhydrazonomethyl-6,8-dimethyl-7-ethoxycarbonyl-1-phthalazone ($R^4$=CH=N—NHCONH$_2$, $R^6$=$R^8$=CH$_3$, $R^7$=C$_2$H$_5$)

decomposed at above 280° C.
mass spectra (m/e): 331, 314, 288, 271.
As the raw material, semicarbazide was used.

EXAMPLE 6

4-isopropylidenehydrazonomethyl-6,8-dimethyl-7-ethoxycarbonyl-1-phthalazone
($R^4$=CH=N—N=C(CH$_3$)$_2$, $R^6$=$R^8$=CH$_2$, $R^7$=C$_2$H$_5$)

To 250 mg of 4-hydrazonomethyl-6,8-dimethyl-7-ethoxycarbonyl-1-phthalazone, 20 ml of ethanol, 1 ml of acetone and 5 drops of glacial acetic acid were added. The resulting mixture was heated on water bath for 2 hours and the reaction mixture was concentrated to about half volume. After cooling, the crystals precipitated were collected by filtration and recrystallized from methanol to give 200 mg of slightly yellowish crystals. m.p. 213°–215° C.

Analysis calculated for $C_{17}H_{20}O_3N_4$ C 62.18, H 6.14, N 17.06, found C 63.30, H 6.12, N 17.24.
mass spectra (m/e): 328, 300, 283, 271.

EXAMPLE 7

4-sec-butylidenehydrazonomethyl-6,8-dimethyl-7-ethoxycarbonyl-1-phthalazone
($R^4$=CH=N—N=C(CH$_3$)C$_2$H$_5$, $R^6$=$R^8$=CH$_3$, $R^7$=C$_2$H$_5$)

By the same manner as in Example 6, but methylethylketone was used instead of acetone, the desired product was obtained in a similar yield.
m.p. 186°–188° C. (recrystallized from methanol)
mass spectra (m/e): 342, 313, 301.

EXAMPLE 8

4-carbamoyl-6,8-dimethyl-7-ethoxycarbonyl-1-phthalazone ($R^4$=CONH$_2$, $R^6$=$R^8$=CH, $R^7$=C$_2$H$_3$)

In 200 ml of concentrated aqueous ammonia, 3 g of 4,7-diethoxycarbonyl-6,8-dimethyl-1-phthalazone was suspended. The suspension was stirred at room temperature for 10 hours. The crystals precipitated were collected by filtration and recrystallized from methanol to give 2.4 g of the desired product.
m.p. 258°–260° C.

Analysis calculated for C$_{14}$H$_{15}$O$_4$N$_3$ C 58.12, H 5.23, N 14.53, found C 58.30, H 5.25, N 14.28, IR spectra ($\nu_{max}^{KBr}$): 3400, 1740, 1670, 1650 cm$^{-1}$; NMR spectra (DMSO-d$_6$): 8.20 (s,1H), 7.80 (s,1H), 7.55 (s,1H), 4.45 (d, J=7Hz, 1H), 4.25 (d, J=7Hz, 1H), 3.25 (s,1H), 2.70 (s,3H), 2.30 (s,3H), 1.40 (t, J=7Hz, 3H).
mass spectra (m/e): 289 (M+), 260, 244, 217.

EXAMPLE 9

4-hydrazinocarbonyl-6,8-dimethyl-7-ethoxycarbonyl-1-phthalazone ($R^4$=CONHNH$_2$, $R^6$=$R^8$=CH$_3$, $R^7$=C$_2$H$_5$)

To 600 mg of 4,7-diethyoxycarbonyl-6,8-dimethyl-1-phthalazone, 2 ml of 85% hydrazine hydrate was added. The resulting mixture was heated at 80° C. on a water bath for one hour. After addition of 20 ml of methanol, the reaction mixture was allowed to stand. The crystals precipitated were collected by filtration and recrystallized from methanol to give 230 mg of the desired product.
m.p. 241°–243° C.

Analysis calculated for C$_{14}$H$_{16}$O$_4$N$_4$ C 55.25, H 5.30, N 18.41, found C 54.87, H 5.27, N 18.45, IR spectra ($\nu_{max}^{KBr}$): 3340, 1710, 1660, 1650 cm$^{-1}$; NMR spectra (DMSO-d$_6$): 12.30 (s,1H), 9.50 (s,1H), 7.75 (s,1H), 4.40 (d, J=7Hz, 1H), 4.20 (d, J=7Hz, 1H), 3,20 (broad, 2H), 2.70 (s, 3H), 2.25 (s, 3H), 1.30 (t, J=7Hz, 3H) mass spectra (m/e): 304 (M+), 273, 259, 245.

EXAMPLE 10

4-N-(β-diethylaminoethyl)carbamoyl-6,8-dimethyl-7-ethoxycarbonyl-1-phthalazone
($R^4$=CONHCH$_2$CH$_2$N(C$_2$H$_5$)$_2$, $R^6$=$R^8$=CH$_3$, $R^7$=C$_2$H$_5$)

To 300 mg of 4,7-diethoxycarbonyl-6,8-dimethyl-1-phthalazone, 1 ml of unsym-N,N-diethylethylenediamine was added. The mixture was heated at 80° C. on water bath with stirring occasionally for two hours. After cooliling, the reaction mixture was added to 40 ml of chloroform. The chloroform layer was washed with water and dried with magnesium sulfate. The resulting solution was concentrated to dryness and the residue was crystallized from ethyl acetate-petroleum ether to give 160 mg of the desired product.
m.p. 161°–162° C.

IR spectra ($\nu_{max}^{KBr}$): 3300, 2950, 1720, 1670, 1640 cm$^{-1}$. NMR spectra (CDCl$_3$)δ: 8.75 (s,1H), 7.75 (broad, 1H), 4.55 (d, J=8Hz, 1H), 4.25 (d, J=8Hz, 1H), 3.55 (d, J=6Hz, 1H), 3.40 (d, J=6Hz, 1H), 2,80 (s,5H), 2.75 (d, J=7Hz, 2H), 2.50 (d, J=7 Hz, 2H), 2.40 (s,3H), 1.40 (t, J=6Hz, 3H), 1.10 (t, J=7Hz, 6H); mass spectra (m/e): 388 (M+), 343.

By a similar manner as in Example 8 to Example 10, the compounds of Example 11 to Example 13 were obtained.

EXAMPLE 11

4-methylhydrazinocarbonyl-6,8-dimethyl-7-ethoxycarbonyl-1-phthalazone ($R^4$=CONHNHCH$_3$, $R^6$=$R^8$=CH$_3$, $R^7$=C$_2$H$_5$) m.p. 215°–216° C. (crystallized from methanol) mass spectra (m/e): 318, 304, 289, 273.

As the raw material, methylhydrazine was used.

EXAMPLE 12

4-[N-(3-dimethylaminopropyl)carbamoyl]-6,8-dimethyl-7-ethoxycarbonyl-1-phthalazone
($R^4$=CONHCH$_2$CH$_2$CH$_2$N(CH$_3$)$_2$, $R^6$=$R^8$=CH$_3$, ($R^7$=C$_2$H$_5$) m.p. 176°–178° C. (crystallized from ethyl acetate-petroleum ether), mass spectra (m/e): 374, 329, 289.

As the raw material, unsym-N,N-dimethyl-trimethylenediamine was used.

EXAMPLE 13

4[N-(3-diethylaminopropyl)carbamoyl]-6,8-dimethyl-7-ethoxycarbonyl-1-phthalazone
($R^4$=CONHCH$_2$CH$_2$CH$_2$N(C$_2$H$_5$)$_2$, $R^6$=$R^8$=CH$_3$, $R^7$=C$_2$H$_5$ m.p. 141°–143° C. (crystallized from ethyl acetate-petroleum ether), mass spectra (m/e): 402, 373, 357, 330.

As the raw material, unsym-N,N-diethyl-trimethylenediamine was used.

EXAMPLE 14

4-(2-hydroxyethyl)carbamoyl-6,8-dimethyl-7-ethoxycarbonyl-1-phthalazone ($R^4$=CONHCH$_2$CH$_2$OH, $R^6$=$R^8$=CH$_3$, $R^7$=C$_2$H$_5$)
m.p. 208°–209° C. (crystallized from methanol)
mass spectra (m/e): 333, 318, 302, 289

As the raw material, 2-aminoethanol was used.

EXAMPLE 15

4-isopropylidenehydrazinocarbonyl-6,8-dimethyl-7-ethoxycarbonyl-1-phthalazone
($R^4$=CONHN=C(CH$_3$)$_2$, $R^6$=$R^8$=CH$_3$, $R^7$=C$_2$H$_5$)

To a solution of 300 mg of 4-hydrazinocarbonyl-6,8-dimethyl-7-ethoxycarbonyl-1-phthalazone and 30 ml of ethanol, 1.5 ml of acetone and 3 drops of glacial acetic acid were added. The mixture was heated under reflux on water bath for one hour. The reaction mixture was concentrated to about ⅓ and the resulted solution was allowed to stand. The crystals precipitated were collected by filtration and recrystallized from methanol to give 280 mg of the desired product. m.p. 215°–217° C.

Analysis calculated for C$_{17}$H$_{20}$O$_4$N$_4$ C 59.29, H 5.85, N 16.27 found C 59.42, H 5.79, N 16.41, IR spectra ($\nu_{max}^{KBr}$): 1720, 1660 cm$^{-1}$ NMR spectra (DMSO-d$_6$)δ: 7.80 (s,1H), 4.45 (d, J=6Hz, 1H), 4.20 (d, J=6Hz, 1H), 3.25 (s,1H), 2.75 (s,3H), 2.30 (s,3H), 2.00 (s,3H), 1.90

(s,3H), 1.30 (t, J=6Hz, 3H); mass spectra (m/e): 344 (M+), 329, 299, 273.

While the present invention has been described in detail with reference to the specific embodiments thereof, it is apparent to one skilled in the art that various changes and modifications can be made therein without departing the scope and the spirit of the present invention.

What is claimed is:

1. A compound of the formula

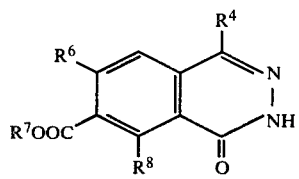

wherein $R^4$ represents a carbamoyl group, a dialkylaminoalkylcarbamoyl group, a hydroxyalkylcarbamoyl group, an alkylidenehydrazinocarbonyl group, a hydrazinocarbonyl group, an alkylhydrazinocarbonyl group, an alkylhydrazonomethyl group, a hydroxyiminomethyl group, a dialkylhydrazonomethyl group, a carbamoylhydrazonomethyl group, an alkylidenehydrazonomethyl group, or a hydrazonomethyl group, $R^6$, $R^7$ and $R^8$ each represent an alkyl group of 1 to 6 carbon atoms, or a pharmaceutically acceptable acid addition salt thereof.

2. The compound of claim 1, which is: 4-N-(β-diethylaminoethyl) carbamoyl-6,8-dimethyl-7-ethoxycarbonyl-1-phthalazone.

3. The compound of claim 1, wherein the alkyl group has 1 to 3 carbon atoms.

4. The compound of claim 1, which is 4-hydrazinocarbonyl-6,8-dimethyl-7-ethoxycarbonyl-1-phthalazone or pharmaceutically acceptable acid addition salt thereof.

5. The compound of claim 1, which is 4-isopropylidenehydrazonomethyl-6,8-dimethyl-7-ethoxycarbonyl-1-phthalazone.

6. The compound of claim 1, which is: 4-hydrazonomethyl-6,8-dimethyl-7-ethoxycarbonyl-1-phthalazone.

7. The compound of claim 1, which is: 4-hydroxyiminomethyl-6,8-dimethyl-7-ethoxycarbonyl-1-phthalazone.

8. The compound of claim 1, which is: 4-dimethyl hydrazonomethyl-6,8-dimethyl-7-ethoxycarbonyl-1-phthalazone.

9. The compound of claim 1, which is: 4-carbamoylhydrazonomethyl-6,8-dimethyl-7-ethoxycarbonyl-1-phthalazone.

10. The compound of claim 1, which is: 4-sec-butylidenehydrazonomethyl-6,8-dimethyl-7-ethoxycarbonyl-1-phthalazone.

11. The compound of claim 1, which is: 4-carbamoyl-6,8-dimethyl-7-ethoxycarbonyl-1-phthalazone.

* * * * *